(12) United States Patent
Maier et al.

(10) Patent No.: US 6,579,705 B2
(45) Date of Patent: Jun. 17, 2003

(54) PROCESS FOR PREPARING NON-PROTEINOGENIC L-AMINO ACIDS

(75) Inventors: Thomas Maier, Dachau (DE); Carsten Gaebert, München (DE)

(73) Assignee: Consortium fur Elektrochemische Industrie GmbH, Munich (DE)

( * ) Notice: Subject to any disclaimer, the term of this patent is extended or adjusted under 35 U.S.C. 154(b) by 0 days.

(21) Appl. No.: 10/104,218

(22) Filed: Mar. 22, 2002

(65) Prior Publication Data

US 2002/0177196 A1 Nov. 28, 2002

(30) Foreign Application Priority Data

Apr. 4, 2001 (DE) .......................................... 101 16 881
May 3, 2001 (DE) .......................................... 101 21 515

(51) Int. Cl.$^7$ ........................... C12P 13/04; C12N 9/88
(52) U.S. Cl. ...................................... 435/106; 435/232
(58) Field of Search ................................ 435/106, 232

(56) References Cited

U.S. PATENT DOCUMENTS 3,974,031 A  8/1976  Yamada et al.

FOREIGN PATENT DOCUMENTS

| DE | 100 46934 | 4/2002 |
|----|-----------|--------|
| EP | 0323068 | 7/1989 |
| EP | 1191106 | 3/2002 |
| JP | 58187198 | 11/1983 |
| JP | 2001061489 | 3/2001 |
| WO | 9901561 | 1/1999 |

OTHER PUBLICATIONS

Ikegami et al "Enzymic Synthesis of Non–Protein Beta--Substituted Alanine and some higher Homologues in Plants" Phytochemistry vol. 35, No. 5 (1994) pp. 1089–1104.*

Choct et al., 1985, Agric. Biol. Chem., 49, pp. 1143–1153.

Yanse et al., 1982, Agric. Biol. Chem., 46 pp. 363–369.

Taylor et al. 1998, Tibtech vol. 16: 412–418.

Drauz 1997, Chimia 51, No. 6 (Jun.).

Flint et al., 1996, The Journal of Biological Chemistry, vol. 271: 16053–16067.

Kitabatake et al., Jan. 2000, Journal of Bacteriology vol. 182, No. 1: 143–145.

Ikegami & Murakoshi, 1994, Phytochemistry vol. 35, No. 5: 1089–1104.

Tai et al. 1995, Biochemistry 34: 12311–12322.

M. K. Gaitonade, 1967, Biochem. J. 104: 627–633.

Saito et al; Biological and Pharmaceutical Bulletin, Tokyo, JP, vol. 20, No. 1, Jan. 1, 1997; pp. 47–53.

Noji Masaaki et al; Biochemical and Biophysical Research Communications; vol. 197, No. 3, 1993, pp. 1111–1117.

Ikegami Fumio et al; Phytochemistry (Oxford), vol. 35; No. 5; 1994; pp. 1089–1104.

Patent Abstracts of Japan, vol. 008, No. 19 (L–207) Jan. 26, 1984 corresp. to JP 58 187198.

Patent Abstracts of Japan, vol. 2000, No. 20, Jul. 10, 2001 corresp. to JP 2001 061489 A.

* cited by examiner

Primary Examiner—Herbert J. Lilling
(74) Attorney, Agent, or Firm—Collard & Roe, P.C.

(57) ABSTRACT

Process is provided for preparing a non-proteinogenic L-amino acid by means of an enzymic biotransformation in which O-acetyl-L-serine is reacted with a nucleophilic compound, while using an O-Acetyl-L-serine sulfhydrylase as catalyst, to give a non-proteinogenic L-amino acid. The process is carried out at a pH in the range between pH 5.0 and 7.4.

24 Claims, 1 Drawing Sheet cysKS1: 5'-gat cga ggt ctc gaa tga gta aga ttt tga aag a-3'

SEQ.ID.NO. 1

FIG. 1 cysKS2: 5'-gat cga ggt ctc ggc gct ctg ttg caa ttc ttt ctc ag-3' SEQ.ID.NO. 2

FIG. 2 cysMS3: 5'-gat cga ggt ctc gaa tga gta cat tag aac aaa c-3 SEQ.ID.NO. 3

FIG. 3 cysMS5: 5'-gat cga ggt ctc ggc gct aat ccc cgc ccc ctg gct aa-3' SEQ.ID.NO.4

FIG. 4

SEQUENCE LISTING

```
<160> NUMBER OF SEQ ID NOS: 5

<210> SEQ ID NO 1
<211> LENGTH: 34
<212> TYPE: DNA
<213> ORGANISM: Artificial Sequence
<220> FEATURE:
<221> NAME/KEY: misc_feature
<223> OTHER INFORMATION: Primer for PCR

<400> SEQUENCE: 1
gatcgaggtc tcgaatgagt aagatttttg aaga                              34

<210> SEQ ID NO 2
<211> LENGTH: 38
<212> TYPE: DNA
<213> ORGANISM: Artificial Sequence
<220> FEATURE:
<221> NAME/KEY: misc_feature
<223> OTHER INFORMATION: Primer for PCR

<400> SEQUENCE: 2
gatcgaggtc tcggcgctct gttgcaattc tttctcag                          38

<210> SEQ ID NO 3
<211> LENGTH: 34
<212> TYPE: DNA
<213> ORGANISM: Artificial Sequence
<220> FEATURE:
<221> NAME/KEY: misc_feature
<223> OTHER INFORMATION: Primer for PCR

<400> SEQUENCE: 3
gatcgaggtc tcgaatgagt acattagaac aaac                              34

<210> SEQ ID NO 4
<211> LENGTH: 38
<212> TYPE: DNA
<213> ORGANISM: Artificial Sequence
<220> FEATURE:
<221> NAME/KEY: misc_feature
<223> OTHER INFORMATION: Primer for PCR

<400> SEQUENCE: 4
gatcgaggtc tcggcgctaa tccccgcccc ctggctaa                          38

<210> SEQ ID NO 5
<211> LENGTH: 8
<212> TYPE: PRT
<213> ORGANISM: Artificial Sequence
<220> FEATURE:
<221> NAME/KEY: PEPTIDE
<222> LOCATION: (1)..(8)
<223> OTHER INFORMATION: StrepTagII affinity peptide for protein
      purification

<400> SEQUENCE: 5

Trp Ser His Pro Gln Phe Glu Lys
1               5
```

PROCESS FOR PREPARING NON-PROTEINOGENIC L-AMINO ACIDS

BACKGROUND OF THE INVENTION

1. Field of the Invention

The invention relates to a process for preparing non-proteinogenic L-amino acids by means of enzymic biotransformation.

2. The Prior Art

Non-proteinogenic amino acids are amino acids which are not used in nature as building blocks for protein biosynthesis and are thereby to be clearly demarcated from the 20 proteinogenic amino acids. Within the meaning of the present invention, the very rare amino acid L-selenocysteine, which does indeed occur in proteins, is classified among the non-proteinogenic amino acids.

Non-proteinogenic amino acids constitute interesting compounds, for example for producing pharmaceutical and agricultural active compounds. They are able, as an active compound or as part of an active compound, to imitate the structure of natural amino acids in a type of molecular mimicry and thereby modulate the natural reaction, for example in the case of receptor interactions. Furthermore, as chiral compounds, they can, quite generally, serve as synthetic building blocks within the context of the "chiral pool".

Present methods for preparing non-proteinogenic amino acids in enantiomerically pure form are for the most part based on syntheses which are elaborate and which, furthermore, usually only permit access to one particular compound. Only a few methods enable different compounds to be prepared by simply replacing a starting compound. In most cases, the syntheses are chemical syntheses which, for their part, usually already proceed from chiral building blocks. Other methods combine the chemical synthesis of racemates with a racemate resolution which is frequently carried out enzymically.

In addition, some enzymic methods which make use of prochiral compounds and which enable non-proteinogenic amino acids to be synthesized stereoselectively have also been described. Thus, it is possible to employ transaminases to prepare various non-proteinogenic amino acids from α-keto acids using L-glutamic acid as the amino donor (Taylor et al. 1998, *TIBTECH* 16: 412–418). Another example is the synthesis of L-tert-leucine using leucine dehydrogenase (Drauz 1997, *Chimia* 51: 310–314).

The patent application DE 10046934 (registered on 21.09.2000 by the same applicant) describes a particularly simple method for preparing non-proteinogenic amino acids by means of direct fermentation of microorganisms. This method uses organisms whose cysteine metabolism is deregulated and which therefore supply a high level of O-acetyl-L-serine. In cysteine metabolism, this compound serves as a biosynthetic precursor of L-cysteine. The latter is formed by substituting the acetate group at the β position with a thiol radical. This reaction, which is termed β substitution, is catalyzed by enzymes of the O-acetyl-L-serine sulfhydrylase class [EC 4.2.99.8]. When nucleophilic substances belonging to particular compound classes (thiols, azoles and/or isoxazolinones) are fed in during the fermentation, these compounds enter into β substitution, thereby achieving the production of non-proteinogenic L-amino acids. The structure of the respective radicals of the amino acids which are prepared are thus dictated by the nucleophilic compound which is supplied.

A problem with this method is that the nucleophilic compounds which are fed in should not be metered in at too high a rate since, otherwise, the compound itself, or the resulting amino acid, can elicit toxic effects on the metabolism of the microorganisms. This applies, in particular, to many thiol compounds since, as redox-active substances, they possess toxicity at higher concentrations. Furthermore, it is very problematical to use thiol compounds in fermentative methods because, when the fermenter is intensively aerated, they tend toward oxidation and, without mechanical provisions, cause a significant degree of obnoxious odor. Because of their high toxicity, it is not possible, either, to feed in azide or cyanide, which are known to enter into β substitution when O-acetyl-L-serine sulfhydrylases are used (Flint et al., 1996, *J. Biol. Chem.* 271: 16053–16067).

SUMMARY OF THE INVENTION

It is an object of the present invention to provide a process for preparing non-proteinogenic L-amino acids, which process makes it possible to use nucleophilic compounds, in particular toxic compounds as well, which are metered in at a high rate.

This object is achieved according to the present invention by means of an enzymic biotransformation method in which O-acetyl-L-serine is reacted with a nucleophilic compound, while using an O-acetyl-L-serine sulfhydrylase as catalyst, to give a non-proteinogenic L-amino acid, which comprises the process being carried out at a pH in the range between pH 5.0 and 7.4.

This process makes it possible to synthesize a large number of non-proteinogenic, enantiomerically pure L-amino acids, some of which are novel, on an industrial scale.

O-Acetyl-L-serine sulfhydrylases are known. They have so far been isolated from a very wide variety of plants and microorganisms. Those which have been investigated to the greatest extent are the corresponding bacterial enzymes isolated from *Salmonella typhimurium*. In this organism, there are two O-acetyl-L-serine sulfhydrylase enzymes, which are designated OASS-A and OASS-B, respectively. The pertinent genes are likewise known and are termed cysK and cysM, respectively. Although the two enzymes possess very similar reaction mechanisms, they only exhibit 45% identity on the basis of their amino acid sequences.

OASS-B (CysM) has been reported to be able, in contrast to OASS-A (CysK), to catalyze a reaction of O-acetyl-L-serine with thiosulfate to give S-sulfocysteine. This reaction plays an important role in the growth of the bacteria when thiosulfate is the sole sulfur source.

Furthermore, comparisons of the sequences of O-acetyl-L-serine genes from various organisms indicate that there are two phylogenetic groups (Kitabatake et al., 2000, *J. Bacteriol.* 182: 143–145). *Salmonella typhimurium* CysK and *Escherichia coli* CysK form a large group together with the O-acetyl-L-serine sulfhydrylases from other Eubacteria, from methanogenic Archaea and from plants. By contrast, *Salmonella typhimurium* CysM and *Escherichia coli* CysM are located in a very small family together with the O-acetyl-L-serine sulfhydrylases from hyperthermophilic Archaea (e.g. Pyrococcus, Sulfolobus and Thermoplasma).

Within the meaning of the present invention, O-acetyl-L-serine sulfhydrylases are distinguished by the fact that they are able to catalyze the synthesis of L-cysteine from O-acetyl-L-serine and sulfide. Both CysM-related and CysK-related enzymes are therefore O-acetyl-L-serine sulfhydrylases within the meaning of the present invention.

Although a few publications show that O-acetyl-L-serine sulfhydrylases from the CysK group exhibit a relatively broad substrate spectrum (Ikegami & Murakoshi, 1994, *Phytochemistry* 35: 1089–1104; Flint et al., 1996, *J. Biol. Chem.* 271:16053–16067), the possibility of using O-acetyl-L-serine sulfhydrylases industrially for producing non-proteinogenic amino acids has not previously been considered.

The crucial reason which has previously stood in the way of using O-acetyl-L-serine sulfhydrylases to implement the enzymic preparation of non-proteinogenic amino acids industrially lies in the fact that O-acetyl-L-serine is unstable precisely in the pH range which corresponds to the activity range of the O-acetyl-L-serine sulfhydrylases.

O-Acetyl-L-serine isomerizes to N-acetyl-L-serine in dependence on the pH. The reaction is irreversible and, for example, at a pH of 7.6 extremely rapid, with rates of $1\% \times min^{-1}$. The rate of reaction falls as the pH is lowered such that the compound is stable at pH 4.0, for example. The mechanism of the reaction is based on an intramolecular, nucleophilic attack of the deprotonated amino group on the carbonyl carbon of the acyl radical (Tai et al. 1995, *Biochemistry* 34: 12311–12322).

By contrast, the pH optimum of O-acetyl-L-serine sulfhydrylases lies in the region of pH 8.0 (Ikegami & Murakoshi, 1994, *Phytochemistry* 35: 1089–1104; Tai et al. 1995, *Biochemistry* 34: 12311–12322) and consequently in a region which is very unfavorable with regard to the isomerization of O-acetyl-L-serine.

For this reason, Ikegami & Murakoshi propose a biomimetic synthesis of non-proteinogenic amino acids using O-acetyl-L-serine, a nucleophilic compound, pyridoxal phosphate and metal ions (preferably $Ga^{2+}$). This reaction can take place in a pH range of from 3.5 to 5.5 and consequently ensures the stability of O-acetyl-L-serine. However, with maximum yields of <45%, the efficiency of this method is not very high. A major disadvantage as compared with the enzymic synthesis is the lack of enantioselectivity.

Another object, which is achieved by the process according to the invention, was, therefore, to provide an enzymic process for preparing enantiomerically pure, non-proteinogenic amino acids which, despite the incompatibility of the O-acetyl-L-serine stability and the enzyme activity optimum, ensures an efficient enzymic turnover (>>45%) in association with a low level of isomerization.

The object was achieved by the process according to the invention since this process is preferably distinguished by the fact that the reaction is carried out below the pH optimum of the O-acetyl-L-serine sulfhydrylases, and the enzyme is used in sufficiently high dosage.

The preferred pH range for preparing non-proteinogenic amino acids within the meaning of the present invention is the pH range between pH 5.0 and 7.4.

The pH range is particularly preferably between pH 6.0 and 7.1.

The pH range is especially preferably between pH 6.0 and 6.99.

The pH is preferably kept constant by regulating it actively in order to counteract the stoichiometric formation of acetic acid as well. The active regulation of the pH is preferably accomplished by means of a measuring and control unit which, when the pH deviates from the required value, resets it by metering in an alkali or acid.

Contrary to the approach adopted in accordance with the invention, the reactions using O-acetyl-L-serine sulfhydrylases for synthesizing non-proteinogenic amino acids which have been previously described in the literature have been carried out in the region of the pH optimum of the O-acetyl-L-serine sulfhydrylases without any active regulation of the pH and solely on an analytical scale. Furthermore, they have without exception used enzymes belonging to the phylogenetic group to which the CysK enzymes belong.

The invention consequently also relates to a process for preparing a non-proteinogenic L-amino acid in which O-acetyl-L-serine is reacted with a nucleophilic compound, while using an O-Acetyl-L-serine sulfhydrylase as catalyst, to give a non-proteinogenic L-amino acid, which comprises using CysM as the O-acetyl-L-serine sulfhydrylase.

An adequately high dosage of the enzyme ensures that sufficient turnover takes place even outside the pH optimum of the enzyme reaction. Such an enzyme concentration is then preferably achieved for the process when the volume activity of the O-acetyl-L-serine sulfhydrylase, $A_{cys}$, is at least 2 units/ml in the mixture. The activity is particularly preferably 2–200 units/ml. The activity is determined using the test described in example 3.

During the course of the present invention, it was possible to observe that O-acetyl-L-serine sulfhydrylases from the phylogenetic group to which the CysM enzymes belong are also outstandingly good enzymes for preparing non-proteinogenic amino acids. Surprisingly, the spectrum of the nucleophilic compounds which are suitable for use as the substrate is even broader than that of the CysK enzymes.

In a particularly preferred embodiment of the invention, the enzyme reaction is conducted as a continuous process. In this case, O-acetyl-L-serine, O-acetyl-L-serine sulfhydrylases and nucleophilic compound are metered in constantly and, at the same time, a solution containing the non-proteinogenic L-amino acid (product solution) is withdrawn from the mixture. The latter preferably takes place such that the volume in the reaction mixture remains the same. The particular advantage of this procedure is that a steady state is set up such that there is a constantly low concentration of O-acetyl-L-serine in the mixture and the isomerization is consequently decreased. Preferably, the concentration of O-acetyl-L-serine in the mixture is adjusted to <1.0 g/l. This value can be controlled by varying the mean dwell time of the solution in the reaction mixture. The reservoir of O-acetyl-L-serine for the continuous reaction is preferably maintained at an acidic pH, preferably at pH 4–5, in order to ensure sufficient stability.

O-Acetyl-L-serine has previously only been available from chemical synthesis, by the acetylation of L-serine, and has been expensive due to the high prices for L-serine. The application DE 10107002, which belongs to the same applicant and which was filed on Feb. 15, 2001, describes a fermentative method for preparing O-acetyl-L-serine. While this application makes available a cost-advantageous production system, there are difficulties with isolating the product from the fermenter broth due to the instability of the O-acetyl-L-serine.

An advantage of the present invention is that an O-Acetyl-L-serine-containing fermenter broth, as is obtained, for example, from a fermentation which is carried out as described in DE 10107002, can be used directly as the O-acetyl-L-serine source in the process according to the invention. This approach is particularly economical and avoids the isolation of an unstable compound.

O-Acetyl-L-serine sulfhydrylases for synthesizing the non-proteinogenic amino acids are preferably prepared using customary recombinant DNA techniques with which the skilled person is familiar.

For this, a gene which encodes an O-Acetyl-L-serine sulfhydrylase is cloned into a suitable vector and a suitable host strain is subsequently transformed. Any microorganism which is accessible to recombinant DNA techniques and which is suitable for fermentatively preparing recombinant proteins is suitable for use as the host strain.

*Escherichia coli* is a preferred microorganism for preparing O-acetyl-L-serine sulfhydrylases.

In principle, it is possible for the recombinant O-acetyl-L-serine sulfhydrylase gene to be integrated into the chromosome or else to be used on a self-replicating plasmid vector.

In the cloning, preference is given to using vectors which already contain genetic elements (e.g. regulatable promoters, terminators) which enable the O-acetyl-L-serine sulfhydrylase gene to be expressed in a controlled and strongly inducible manner. Particular preference is given to plasmid vectors which are present in high copy number, such as the *Escherichia coli* vectors pUC18, pBR322, pACYC184 and their derivatives. Examples of suitable strongly inducible promoters are the lac, tac, trc, lambda $P_L$, ara and tet promoters.

O-Acetyl-L-serine sulfhydrylases are produced, for example, by cultivating a recombinant microorganism strain by means of fermentation. In this connection, use is made of propagating methods which are known to a skilled person, with the methodological parameters having to be adapted to the given microorganism strain. Both complete media and minimal media can be used as nutrient media. It is possible to use either a batch process or a fed-batch process. When inducible promoter systems are used, expression of the O-acetyl-L-serine sulfhydrylase gene is switched on at a suitable point in time by adding an appropriate inducer. Following an adequate production phase, the O-acetyl-L-serine sulfhydrylase-containing cells are harvested using known methods (e.g. centrifugation).

The O-acetyl-L-serine sulfhydrylase enzyme which is prepared in this way can be isolated using customary methods of protein purification. In this connection, it is possible to use both classical methods (e.g. precipitation, ion exchange chromatography, hydrophobic interaction chromatography and isoelectric focussing) and modern affinity chromatography employing "affinity tags". Sequences which encode these affinity tags can be fused to the coding region when the gene is cloned, thereby giving rise to fusion proteins which contain the corresponding affinity tag. These proteins are then isolated in a one-step purification. An example of a suitable combination of affinity tag and affinity purification is the Strep-Tag and Streptavidin affinity chromatography, which combination can be purchased from IBA, Göttingen, Germany.

It is possible to use an O-Acetyl-L-serine sulfhydrylase in purified form in the process according to the invention. However, in addition to the reaction in solution, it is also possible to immobilize the enzyme on a support. Appropriate methods belong to the state of the art.

However, it is not absolutely necessary to isolate the O-acetyl-L-serine sulfhydrylase for preparing non-proteinogenic amino acids. It is also possible to employ microorganism cells, which possess O-acetyl-L-serine sulfhydrylase activity, directly in the process according to the invention. Examples of such microorganism strains are the *Escherichia coli* strains DH5α/pFL145 and BLR21(DE3)/pLE4. They are described in examples 1 and 2 and have been deposited in the Deutsche Sammlung für Mikroorganismen und Zellkulturen [German collection of microorganisms and cell cultures], DSMZ, in Braunschweig under the Nos. DSM 14088 and 14089, respectively.

In this variant of the process according to the invention, O-acetyl-L-serine is biotransformed into a non-proteinogenic L-amino acid using resting cells. In this connection, the penetration of O-acetyl-L-serine and a nucleophilic compound into the cells is just as much ensured as the release of the reaction product, i.e. the non-proteinogenic L-amino acid, by the cells.

If desired, transfer of material between the interior of the cell and the reaction medium can be increased by treating the cells with substances which cause the cells to become permeabilized. These substances, for example chloroform or toluene, and their use are known to the skilled person.

In a preferred embodiment of the process, a non-proteinogenic amino acid is formed by the reaction of O-acetyl-L-serine with a nucleophilic compound, while using an O-Acetyl-L-serine sulfhydrylase as catalyst, with the O-acetyl-L-serine sulfhydrylase being present intracellularly in a microorganism.

Particular preference is given to preparing non-proteinogenic L-amino acids by reacting fermentatively obtained, non-purified O-acetyl-L-serine with a nucleophilic compound, while using an O-Acetyl-L-serine sulfhydrylase as catalyst, with the O-acetyl-L-serine sulfhydrylase being present intracellularly in a microorganism.

The nucleophilic compounds which are used in the process according to the invention for the β substitution which is catalyzed by O-acetylserine sulfhydrylases are preferably compounds which contain a radical which is selected from the group consisting of Particular preference is given to adding, to the reaction mixture, a nucleophilic compound which is selected from the group consisting of the following compounds:

thiosulfates thiols of the general formula (1):

where $R^1$ is a monovalent substituted or unsubstituted alkyl, alkoxy, aryl or heteroaryl radical having from 1 to 15 C atoms;

selenides selenols of the general formula (2)

where $R^1$ has the meaning given for formula (1), azides cyanides azoles of the general formula (3) or (4):

-continued (4)

$$\begin{array}{c} R^2 \\ \diagdown \\ C^1 \\ \| \\ C^2 \\ \diagup \\ R^3 \end{array} \begin{array}{c} H \\ | \\ N \\ \diagdown \\ N \\ \diagup \\ X \end{array}$$

where X and Y are identical or different and are $CR^4$ or N, and $R^4$ is —H, —COOH, —OH, —$NH_2$, —$NO_2$, —SH, —$SO_3^-$, —F, —Cl, —Br, —I, $C_1$–$C_5$-alkylcarbonyl- and also their esters, amides or salts, or $R^1$, and $R^1$ has the meaning given for formula (1), and where $R^2$ and $R^3$ are identical or different and are $R^4$ or where $C^1$ and $C^2$ in formula (4) are linked, in place of the substituents $R^2$ and $R^3$, by means of a bridge [—$CR^5R^6$—]$_a$, where a is 1, 2, 3 or 4, to form a ring, where $R^5$ and $R^6$ are identical or different and are $R^4$, and one or more non-adjacent groups [—$CR^5R^6$—] can be replaced with oxygen, sulfur or an imino radical which is optionally substituted by $C_1$–$C_5$-alkyl-, and two adjacent groups [—$CR^5R^6$—] can be replaced with a group [—$CR^5$=$CR^6$—] or with a group [—$CR^5$=N—], isoxazolinones of the general formula (5) or (6):

(5)

$$\begin{array}{c} R^2 \\ \diagdown \\ C \\ \| \\ X \\ \diagup \\ \end{array} \begin{array}{c} H \\ | \\ N \\ \diagdown \\ O, \\ \diagup \\ C \\ \| \\ O \end{array}$$

(6)

$$\begin{array}{c} R^2 \\ \diagdown \\ C^1 \\ \| \\ C^2 \\ \diagup \\ R^3 \end{array} \begin{array}{c} H \\ | \\ N \\ \diagdown \\ O \\ \diagup \\ C^3 \\ \| \\ O \end{array}$$

where X, $R^1$, $R^2$ and $R^3$ have the meaning which has already been given, and where $C^1$ and $C^2$ in formula (6) can be linked, in place of the substituents $R^2$ and $R^3$, by means of a bridge as defined for formula (4) to form a ring.

Examples of thiosulfates are sodium thiosulfate, potassium thiosulfate and ammonium thiosulfate.

Examples of thiols are compounds selected from the group consisting of 2-mercaptoethanol, 3-mercaptopropanol, 3-mercaptopropionic acid, 3-mercapto-1-propanesulfonic acid, mercaptoethanesulfonic acid, 2-mercaptoethylamine, thioglycolic acid, thiolactic acid, thioacetic acid, mercaptosuccinic acid, mercaptopyruvic acid, dithiothreitol, dithioerythritol, 1-thioglycerol, thiophenol, 4-fluorothiophenol, 4-chlorothiophenol, 4-mercaptophenol, p-thiocresol, 5-thio-2-nitrobenzoic acid, 2-mercaptothiazole, 2-mercaptothiazoline, 2-mercaptoimidazole, 3-mercapto-1,2,4-triazole, 2-thiophenethiol, 2-mercaptopyridine, 2-mercaptopyrimidine, 2-thiocytosine, 2-mercaptonicotinic acid, 2-mercapto-1-methylimidazole, 2-mercaptobenzothiazole, 2-mercaptobenzoxazole and 6-mercaptopurine.

Examples of selenols are compounds selected from the group consisting of methylselenol, ethylselenol, propylselenol and phenylselenol.

Examples of azides are sodium azide, potassium azide and ammonium azide.

Examples of cyanides are potassium cyanide, sodium cyanide and ammonium cyanide.

Examples of azoles are compounds selected from the group consisting of 1,2-pyrazole, 3-methylpyrazole, 4-methylpyrazole, 3,5-dimethylpyrazole, 3-aminopyrazole, 4-aminopyrazole, pyrazole-4-carboxylic acid, pyrazole-3,5-dicarboxylic acid, 1,2,3-triazole, 1,2,4-triazole, 3-amino-1,2,4-triazole, 1,2,3,4-tetrazole, indazole, indazole-3-carboxylic acid, indazole-5-carboxylic acid, 5-aminoindazole, benzotriazole, benzotriazole-5-carboxylic acid, 5-aminobenzotriazole, aminopyrazolopyrimidine, 8-azaguanine and 8-azaadenine.

Examples of isoxazolinones are compounds selected from the group consisting of isoxazolin-5-one, 3-methylisoxazolin-5-one, 4-methylisoxazolin-5-one, 4,5-dimethylisoxazolin-2-one and 1,2,4-oxadiazolidine-3,5-dione.

The concentration of the nucleophilic compound in the mixture is preferably selected such that the compound is present in a concentration which is equimolar with that of the O-acetyl-L-serine.

The reaction temperature is preferably selected to be between 5° C. and 70° C. The temperature range which is particularly preferred is between 20° C. and 40° C.

Water is preferably used as the solvent for the reaction.

The reaction products which are formed are preferably L-amino acids of the general formula (7) in the L configuration (7)

$$H_2N-\underset{\underset{Z}{\overset{|}{CH_2}}}{\overset{COOH}{\underset{|}{C}}}-H$$

where Z is a monovalent radical selected from the formulae (8) to (19)

(8)

—S—$SO_3^-$, (9)

—S—$R^1$, (10)

—Se—H, (11)

—Se—$R^1$, (12)

—N=$N^+$=$N^-$, (13)

—C≡N, (14)

$$\begin{array}{c} R^2 \\ \diagdown \\ C \\ \| \\ Y \end{array} \begin{array}{c} | \\ N \\ \diagdown \\ N, \\ \diagup \\ X \end{array}$$

and the esters, ethers or salts thereof, and $R^1$, $R^2$, $R^3$, $R^4$, X and Y have the meaning which has already been given for the formulae (1) to (6).

Preference is given to isolating a soluble non-proteinogenic L-amino acid from the culture supernatant after the process according to the invention has been terminated and after the preferably aqueous solution has been separated, using known methods, into biomass and a culture supernatant. Such methods for isolating amino acids are likewise known to the skilled person. They comprise, for example, filtration, centrifugation, extraction, adsorption, ion exchange chromatography, precipitation and crystallization. In the case of a difficultly soluble non-proteinogenic amino acid, preference is given to carrying out a grading centrifugation, as is known to the skilled person, with the biomass if at all possible remaining in the centrifugation supernatant. The product which has been separated off is preferably dissolved and reprecipitated using standard methods.

BRIEF DESCRIPTION OF THE DRAWINGS

Other objects and features of the present invention will become apparent from the following detailed description considered in connection with the accompanying drawings. It is to be understood, however, that the drawings are designed as an illustration only and not as a definition of the limits of the invention. In the drawings.

DETAILED DESCRIPTION OF THE PREFERRED EMBODIMENTS

The following examples serve to clarify the invention.

EXAMPLE 1

Figure 1:
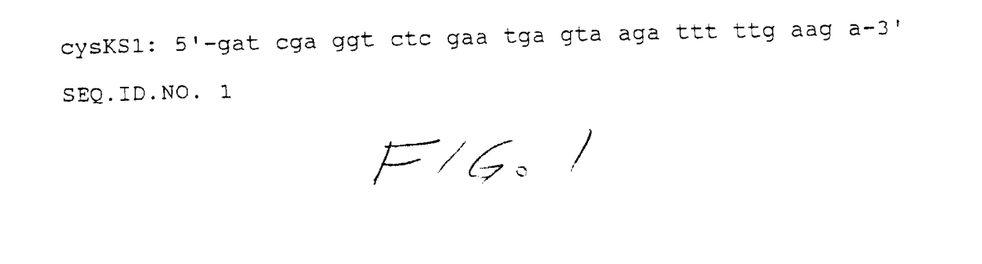
FIG. 1 shows the nucleotide bases for cysKS1.
Figures 2, 3:
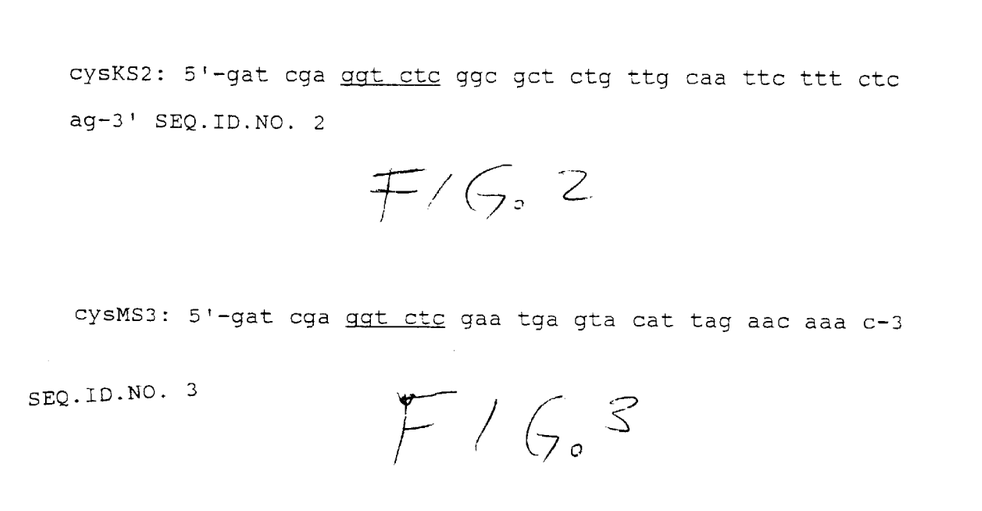
FIG. 2 shows the nucleotide bases for cysKS2.
FIG. 3 shows the nucleotide bases for cysMS3.
Figure 4:
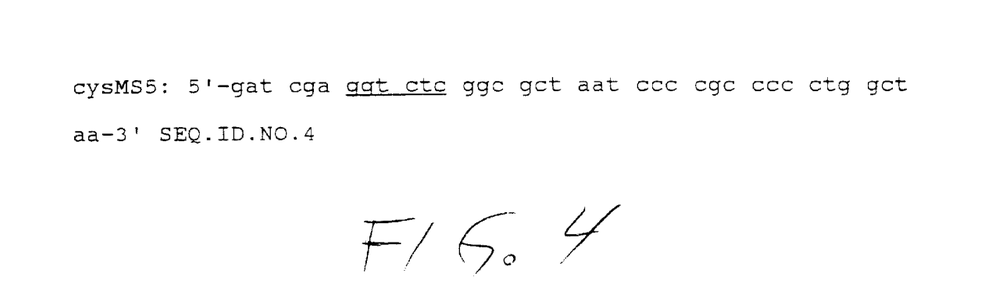
FIG. 4 shows the nucleotide bases for cysMS5.

Cloning the *Escherichia coli* cysK and cysM Genes as Fusion Genes Containing StrepTag Sequences In order to clone the *Escherichia coli* cysK and cysM genes, polymerase chain reactions were first of all carried out using the following phosphorothioate-protected oligonucleotide primer pairs and employing the Pwo DNA polymerase.

cysKS1: (See FIG. 1) SEQ.ID.NO. 1
cysKS2: (See FIG. 2) SEQ.ID.NO. 2 and
cysMS3: (See FIG. 3) SEQ.ID.NO. 3
cysMS5: (See FIG. 4) SEQ.ID.NO. 4

In this connection, cleavage sites for the restriction endonuclease BsaI (underlined nucleotides) were introduced by way of the primer sequences. Chromosomal DNA from *E. coli* W3110 (ATTC 27325) served as a template. The resulting amplificates were digested with the restriction enzyme BsaI and subsequently cloned into the Eco31I-treated vector pASK-IBA3 (Institut für Bioanalytik [Institute for Bioanalysis], Göttingen, Germany). This vector enables a gene to be cloned as a gene fusion which has a sequence at the 3' end which encodes an affinity peptide (WSHPQFEK SEQ.ID.NO. 5) which is designated StrepTagII. Use of the tet promoter to express gene fusion results in a protein which possesses a C-terminal StrepTagII tag. The latter can be used for isolating the protein since StrepTagII mediates binding to Streptavidin columns.

EXAMPLE 2

Purifying the CysK and CysM Proteins

Using the cysM-StrepTag construct (pFL145), it was possible to obtain very good gene expression in the *E. coli* strain DH5α (Clonetech, Heidelberg, Germany). Propagation and expression were carried out in accordance with the instructions provided by the Institut für Bioanalytik company, Göttingen, Germany. The strain DH5α/pFL145 was deposited in the Deutsche Sammlung für Mikroorganismen und Zellkulturen [German collection of microorganisms and cell cultures], DSMZ, in accordance with the Budapest Treaty, under number DSMZ 14088. By contrast, expression was only very weak in the case of the cysK-Streptag construct (pLE1). However, in this case (pLE4), good formation of the gene product was achieved by recloning the gene fusion, as an XbaI/HindIII fragment, into a vector containing the T7 promoter (pRSET5a) (Stratagene, Heidelberg, Germany) and expressing it in the strain BLR21 (DE3) (Novagen, Darmstadt, Germany). The strain BLR21 (DE3)/pLE4 was deposited in the Deutsche Sammlung für Mikroorganismen und Zellkulturen, DSMZ, in accordance with the Budapest Treaty, under the number DSMZ 14089. The CysK and CysM proteins were isolated by affinity chromatography on Streptavidin columns, with this procedure being in principle carried out in accordance with the manufacturer's instructions as supplied by the Institut für Bioanalytik company, Göttingen, Germany. When 250 ml of culture were used, the yield was 3 mg of purified CysK protein or 4.5 mg of purified CysM protein, respectively. On account of the pyridoxal phosphate cofactor, both the proteins exhibited a marked yellow coloration and had an absorption maximum at 420 nm.

EXAMPLE 3

Determining the Enzyme Activity

The activity of O-acetyl-L-serine sulfhydrylases is measured by detecting the "natural" reaction product L-cysteine (Cys) or alternatively, in the case of CysM, also by detecting the reaction product as S-sulfo-L-cysteine (S-Cys). Both products can be detected very specifically and very sensitively using the test described by Gaitonde (1967, *Biochem. J.* 104: 627–633). Separate standard curves had to be calibrated for both compounds since the color complex with sulfocysteine is of lower intensity.

A typical test mixture contained 10 mM O-acetyl-serine (added from a 200 mM stock solution in 500 mM sodium succinate buffer, pH 5.5), 10 mM sodium sulfide or sodium thiosulfate, 100 mM potassium phosphate buffer, pH 7.0, and 5 μg of purified enzyme/ml, and is incubated at 37° C. The specific activity, A, is given in units/mg of protein, i.e. in μmol of product×min$^{-1}$×mg$^{-1}$ of protein. $A_{cys}$ denotes the specific activity of the formation of cysteine using sulfide. $A_{S\text{-}Cys}$ denotes the specific activity of the formation of S-sulfocysteine using thiosulfate. The specific activities using the proteins isolated in example 2 were:

CysK: $A_{cys}$ 140 units/mg

CysM: $A_{cys}$ 199 units/mg

CysM: $A_{S\text{-}cys}$ 145 units/mg

When determining the activity of O-acetylserine sulfhydrylases in resting cells, the optical density of a cell suspension was first of all adjusted to 20.0 (measured at 600 nm). The cells were then permeabilized by adding chloroform to a concentration of 10% by vol. and the mixture was incubated at room temperature for 5 min. For the enzyme test, the optical density was then adjusted to 1.0 and the reaction with O-acetyl-L-serine and sulfide or thiosulfate was then carried out using the cells as described above. The specific activity of the cells, A, in this connection is given in μmol×min$^{-1}$×(ml of cell suspension having an optical density of 1.0 at 600 nm)$^{-1}$; in abbreviated form: units/ml OD.

EXAMPLE 4

Investigating the Catalytic Possibilities of the O-acetyl-L-serine Sulfhydrylases CysK and CysM In order to use the O-acetyl-L-serine sulfhydrylases to prepare non-proteinogenic amino acids, other nucleophilic compounds were used in the reaction in place of sulfide or thiosulfate. In order to detect them, a precolumn derivatization for amino acids was carried out using ortho-phthaldialdehyde. Using this method, it was possible to carry out a broad screening for suitable nucleophilic substrates.

The mixtures contained 4 mM O-acetyl-L-serine (added from a 200 mM stock solution in 500 mM Nasuccinate buffer, pH 5.5), 20 mM nucleophilic compound, 100 mM K phosphate buffer, pH 7.0, and 5 μg of purified enzyme/ml. The reaction was stopped with 1/100th the volume of acetic acid (96% v/v) and analyzed by HPLC using a HP aminoquant column (200 mm×2.1 mm) in accordance with the manufacturer's instructions supplied by Hewlett Packard, Waldbronn, Germany.

In order to characterize the products which were formed, the molecular masses were established using HPLC-MS. A Luna C18 column (Phenomenex, Aschaffenburg, Germany) was used for this purpose, with formic acid (0.1% v/v) being employed as the mobile phase. The ionization was carried out in the positive electrospray mode.

The following table shows the reactivity of the two enzymes, i.e. CysK and CysM, toward various nucleophilic compounds, and the masses which were determined in the HPLC-MS analysis (MH+).

| Nucleophilic compound (or salt) | CysK * | CysM * | Product | MH+ |
|---|---|---|---|---|
| Mercaptoethanol | +++ | +++ | S-Hydroxyethyl-L-cysteine | 166 |
| Dithiothreithol | +++ | +++ | S-Mercaptodihydroxybutyl-L-cysteine | 242 |
| Thiophenol | ++ | +++ | S-Phenyl-L-cysteine | 198 |
| 2-Mercaptothiazole | ++ | +++ | Thiazol-2-yl-L-cysteine | 205 |
| 3 Mercapto-1,2,4-triazole | + | +++ | 1,2,4-Triazol-3-yl-L-cysteine | 189 |
| Sodium selenide | +++ | +++ | L-Selenocysteine | 170 |
| Phenylselenol | ++ | +++ | Phenyl-L-selenocysteine | 246 |
| Sodium azide | +++ | +++ | Azido-L-alanine | 131 |
| Potassium cyanide | +++ | +++ | Cyano-L-alanine | 115 |
| 1,2-Pyrazole | ++ | ++ | 1,2-Pyrazolyl-L-alanine | 156 |
| 1,2,4-Triazole | +++ | ++ | 1,2,4-Triazolyl-1-L-alanine | 157 |
| 1,2,3,4-Tetrazole | +++ | ++ | 1,2,3,4-Tetrazol-2-yl-L-alanine | 158 |
| 1,2,3-Benzotriazole | ++ | + | 1,2,3-Benzotriazol-2-ylalanine | 207 |
| 5-Carboxy-1,2,3-benzotriazole | ++ | + | 5-Carboxy-1,2,3-benzotriazol-2-yl-alanine | 242 |
| 8-Azaguanine | − | + | Azaguan-8-yl-L-alanine | 240 |
| 1,2,4-Oxadiazo-lidine-3,5-dione | − | + | 1,2,4-Oxadiazolidine-dionyl-L-alanine | 190 |

*+++ conversion greater than 70% after 30 min, ++ conversion greater than 40% after 30 min, + conversion greater than 10% after 30 min, − conversion less than 5% after 30 min.

EXAMPLE 5

Preparing the O-acetyl-L-serine Sulfhydrylase CysM by Fermentation

As a preliminary culture for the fermentation, 20 ml of LB medium (10 g of tryptone/l, 5 g of yeast extract/l, 10 g of NaCl/l), which additionally contained 100 mg of ampicillin/l, were inoculated with the strain DH5α/pFL145 (see above) and incubated overnight, in a shaker, at 30° C. and 150 rpm. Subsequently, the entire mixture was transferred into 100 ml of SM1 medium (12 g of $K_2HPO_4$/l; 3 g of $KH_2PO_4$/l; 5 g of $(NH_4)_2SO_4$/l; 0.3 g of $MgSO_4 \times 7$ $H_2O$/l; 0.015 g of $CaCl_2 \times 2$ $H_2O$/l; 0.002 g of $FeSO_4 \times 7$ $H_2O$/l; 1 g of $Na_3$citrate×2 $H_2O$/l; 0.1 g of NaCl/l; 1 ml of trace element solution/l, with this solution consisting of 0.15 g of $Na_2MoO_4 \times 2$ $H_2O$/l; 2.5 g of $Na_3BO_3$/l; 0.7 g of $CoCl_2 \times 6$ $H_2O$/l; 0.25 g of $CuSO_4 \times 5$ $H_2O$/l; 1.6 g of $MnCl_2 \times 4$ $H_2O$/l; 0.3 g of $ZnSO_4 \times 7$ $H_2O$/l) which was supplemented with 5 g of glucose/l; 0.5 mg of vitamin $B_1$/l and 100 mg of ampicillin/l. The further incubation of the preliminary culture took place at 30° C. for 8 hours and at 150 rpm.

The fermenter employed was a Biostat M appliance which was supplied by Braun Biotech (Melsungen, Germany) and which had a maximum culture volume of 2 l. The fermenter containing 900 ml of fermentation medium (15 g of glucose/l; 10 g of tryptone/l; 5 g of yeast extract/l; 5 g of $(NH_4)_2SO_4$/l; 1.5 g of $KH_2PO_4$/l; 0.5 g of NaCl/l; 0.3 g of $MgSO_4 \times 7$ $H_2O$/l; 0.015 g of $CaCl_2 \times 2$ $H_2O$/l; 0.075 g of $FeSO_4 \times 7$ $H_2O$/l; 1 g of $Na_3$citrate×2 $H_2O$/l and 1 ml of trace element solution/l, see above, 5 mg of vitamin B1/l and 100 mg of ampicillin/l, adjusted to pH 7.0 with 25% ammonia) was inoculated with the above-described preliminary culture (optical density of approx. 2 at 600 nm). During the fermentation, the temperature was set at 32° C. and the pH was kept constant at a value of 7.0 by metering in 25% v/v ammonia. The culture was gassed with sterilized compressed air at 1.5 vol/vol/min and stirred with a rotational stirrer speed of 200 rpm. After the oxygen saturation had fallen to a value of 50%, the rotational speed was increased to a value of 1 200 rpm, by way of a monitoring device, in order to maintain 50% oxygen saturation (determined using a $pO_2$ probe which was calibrated to 100% saturation at 900 rpm). A 56% w/v solution of glucose was metered in as soon as the glucose concentration in the fermenter had fallen from the initial value of 15 g/l down to approx. 5–10 g/l. The feeding took place at a flow rate of 3–6 ml/h, with the glucose concentration in the fermenter being kept at between 0.5 and 10 g/l. The glucose was determined using a glucose analyzer supplied by YSI (Yellow Springs, Ohio, USA). When an optical density of 30 had been reached, enzyme production was induced by adding 3 mg of tetracycline/l. The duration of the induction was 7 hours. After this time, samples were removed and the cells were separated off from the culture medium by centrifugation and washed. The resulting cell suspension was analyzed as described in example 3. The O-acetylserine sulfhydrylase activity measured with thiosulfate, $A_{S-Cys}$, was 12 units/ml OD.

The cells were harvested by centrifugation, shock-frozen in liquid nitrogen and stored at −20° C.

EXAMPLE 6

Preparing the O-acetyl-L-serine Sulfhydrylase CysK by Fermentation

In principle, the procedure for preparing the CysK enzyme was the same as that described in example 5. However, the strain BLR21(DE3)/pLE4 was used in this case. Feeding with a 60% (v/v) solution of glycerol was started after the initially introduced 15 g of glucose/l had been consumed. The flow rate was 9.5 ml/h. At the same time, production of the enzyme was induced by adding 0.4 mM isopropyl-β-thiogalactoside (IPTG). After an induction time of 21 hours, samples were removed and the cells were separated off from the culture medium by centrifugation and washed. The resulting cell suspension was analyzed as described in example 3. The specific O-acetylserine sulfhydrylase activity measured with sulfide, $A_{Cys}$, was 2 units/ml OD. The cells were harvested by centrifugation, shock-frozen in liquid nitrogen and stored at −20° C.

EXAMPLE 7

Enzymic Preparation of S-phenyl-L-cysteine Using Resting Cells

O-acetyl-L-serine hydrochloride (Sigma, Deisenhofen, Germany) was first of all dissolved in 100 ml of water in a temperature-controlled vessel equipped with a pH probe and pH control such that a final concentration of 200 mM (29.4 g/l) O-acetyl-L-serine was obtained. After that, 200 mM thiophenol was added while stirring. Subsequently, the mixture was rapidly brought to a pH of 6.7 by titrating with 5 M NaOH and a cell suspension of the CysM production strain DH5α/pFL145 was immediately mixed in. The cell suspension had a specific activity, $A_{S-Cys}$, of 12 units/ml OD. The optical density (measured at 600 nm) of the cells in the mixture was 2.0 and consequently the $A_{S-Cys}$ value of the O-acetylserine activity was 24 units/ml. During the reaction, the pH was kept constant by metering in 5 M NaOH by way of the pH control system.

A white precipitate was observed to be formed during the reaction. After 30 min, a sample was removed and treated with 1% (v/v) acetic acid. The precipitate was separated off by centrifugation, dissolved in an equal volume of 21% (v/v) phosphoric acid and analyzed by HPLC. The centrifugation supernatant was also chromatographed. The analysis was carried out by means of reversed phase HPLC on a LUNA 5μ C18(2) column (Phenomenex, Aschaffenburg, Germany). Dilute phosphoric acid (0.1 ml of conc. phosphoric acid/l), at a flow rate of 0.5 ml/min, was used as the eluent. The content of S-phenyl-L-cysteine was 1.6 g/l in the supernatant and 24.8 g/l in the precipitate. This corresponds to a total reaction yield of 67% based on O-acetyl-L-serine. The preparation was also carried out with the O-acetylserine sulfhydrylase employed being reduced to 12 and 2 units/ml, respectively. However, this led to the enzyme reaction slowing down and, because of the isomerization of the O-acetyl-L-serine, to decreased yields of 52 and 15%, respectively.

EXAMPLE 8

Enzymic Preparation of S-phenyl-L-cysteine Using O-acetyl-L-serine-containing Fermenter Broth and Resting Cells Instead of using O-acetyl-L-serine as a pure substance, this experiment was carried out in an O-Acetyl-L-serine-containing fermenter broth. This broth was obtained by a fermentation as described in patent application DE 10107002. At the end of the fermentation, the pH was adjusted to 4.0 with 21% (v/v) phosphoric acid in order to stabilize the O-acetyl-L-serine. The cells were separated off by centrifugation and the fermenter broth was brought to a concentration of 30 g of O-acetyl-L-serine/l by evaporation. Subsequently, 200 mM thiophenol and, after titration to pH 6.7, cells of the CysM production strain DH5α/pFL145 were admixed with 100 ml of the broth. The $A_{S-Cys}$ activity was 24 units/ml. After that, the further procedure was as described in example 7. The yield based on O-acetyl-L-serine was 65%. An identical mixture containing cells of the CysK production strain BLR21(DE3)/pLE4 gave a yield of 72% when an $A_{Cys}$ of 38 units/ml was employed.

EXAMPLE 9

Continuous Enzymic Preparation of S-phenyl-L-cysteine Using O-acetyl-L-serine-containing Fermenter Broth and Resting Cells An aim of the conduct of the reaction is to achieve turnovers which are as high as possible based on the expensive and unstable starting compound O-acetyl-L-serine. A continuous process was worked out in order to ensure this. In this process the procedure is initially as described in example 8 apart from the fact that the CysM activity, $A_{S-Cys}$, employed was increased to 48 units/ml. After a reaction time of 20 min, O-acetyl-L-serine-containing fermenter broth (30 g/l), thiophenol and a cell suspension of the CysM production strain DH5α/pFL145 (240 OD at 600 nm, in potassium phosphate buffer, pH 7.0) were added by way of metering units. The flow rates were 150, 2.5 and 3 ml/h, respectively. At the same time, the continuous removal of product solution from the reaction vessel, at a flow rate of 155. 5 ml/h, was started. The flow rates were selected such that the reaction volume in the reactor remained constant and a mean dwell time in the reactor was 30 min. Using this procedure, a steady state was established in the mixture with a constant O-acetyl-L-serine concentration of 1.0 g/l. As a consequence of this low concentration, at which the enzyme still possesses very good activity because of its KM value being even lower, it was possible to successfully minimize the isomerization to N-acetyl-L-serine. The reaction yield based on O-acetyl-L-serine was 85%.

EXAMPLE 10

Enzymic Preparation of azido-L-alanine Using O-acetyl-L-serine-containing Fermenter Broth and Resting Cells The procedure followed in this example was in principle the same as that described in example 8 using CysM-containing cells. 200 mM sodium azide were used instead of thiophenol. After a reaction time of 30 min, using cells corresponding to an activity of 72 units/ml in the mixture, the conversion was determined to be 45%.

EXAMPLE 11

Enzymic Preparation of Cyano-L-alanine Using O-acetyl-L-serine-containing Fermenter Broth and Resting Cells The procedure followed in this example was in principle the same as that described in example 8 using CysM-containing cells. 200 mM potassium cyanide were used instead of thiophenol. The cyanide was only added after the pH of the mixture had been adjusted to 6.7. After a reaction time of 30 min, using cells corresponding to an activity of 72 units/ml in the mixture, the conversion was determined to be 65%.

EXAMPLE 12

Enzymic Preparation of S-sulfo-L-cysteine Using O-acetyl-L-serine-containing Fermenter Broth and Resting Cells The procedure followed in this example was in principle the same as that described in example 8 using CysM-containing cells. 200 mM sodium thiosulfate were used instead of thiophenol. After a reaction time of 30 min, using cells corresponding to an activity of 16 units/ml in the mixture, the conversion was determined to be 91%.

EXAMPLE 13

Enzymic Preparation of S-thiazol-2-yl-L-cysteine Using O-acetyl-L-serine-containing Fermenter Broth and Resting Cells The procedure followed in this example was in principle the same as that described in example 8 using CysM-containing cells. 200 mM 2-mercaptothiazole were used instead of thiophenol. After a reaction time of 30 min, using cells corresponding to an activity of 72 units/ml in the mixture, the conversion was determined to be 62%.

EXAMPLE 14

Enzymic Preparation of S-1,2,4-triazol-3-yl-L-cysteine Using O-acetyl-L-serine-containing Fermenter Broth and Resting Cells The procedure followed in this example was in principle the same as that described in example 8 using CysM-containing cells. 200 mM 3-mercapto-1,2,4-triazole were used instead of thiophenol. After a reaction time of 30 min, using cells corresponding to an activity of 72 units/ml in the mixture, the conversion was determined to be 74%.

EXAMPLE 15

Enzymic Preparation of seleno-L-cysteine Using O-acetyl-L-serine-containing Fermenter Broth and Resting Cells The procedure followed in this example was in principle the same as that described in example 8 using CysM-containing cells. 200 mM sodium selenide were used instead of thiophenol. The sodium selenide was prepared by reducing sodium selenite with sodium borohydride. After a reaction time of 30 min, using cells corresponding to an activity of 72 units/ml in the mixture, the conversion was determined to be 75%.

EXAMPLE 16

Enzymic Preparation of Phenyl-seleno-L-cysteine Using O-acetyl-L-serine-containing Fermenter Broth and Resting Cells The procedure followed in this example was in principle the same as that described in example 8 using CysM-containing cells. 200 mM phenylselenol were used instead of thiophenol. After a reaction time of 30 min, using cells corresponding to an activity of 72 units/ml in the mixture, the conversion was determined to be 62%.

EXAMPLE 17

Enzymic Preparation of 1,2,4-triazol-1-yl-L-alanine Using O-acetyl-L-serine-containing Fermenter Broth and Resting Cells The procedure followed in this example was in principle the same as that described in example 8. 200 mM 1,2,4-triazole were used instead of thiophenol. For this reaction, the cells were permeabilized by treating them with 10% (v/v) chloroform. After a reaction time of 30 min, using cells corresponding to an activity of 72 units/ml in the mixture, the conversion was determined to be 48%.

EXAMPLE 18

Enzymic Preparation of 5-carboxy-1,2,3-benzo-triazol-2-yl-L-alanine Using O-acetyl-L-serine-containing Fermenter Broth and Resting Cells The procedure followed in this example was in principle the same as that described in example 8. 200 mM 5-carboxy-1,2,3-benzotriazole were used instead of thiophenol. For this reaction, the cells were permeabilized by treating them with 10% chloroform. After a reaction time of 30 min, using cells corresponding to an activity of 72 units/ml in the mixture, the conversion was determined to be 54%.

EXAMPLE 19

Enzymic Preparation of 1,2,4-oxadiazolidine-3,5-dionyl-L-alanine (=Quisqualic Acid) Using O-acetyl-L-serine-containing Fermenter Broth and Resting Cells The procedure followed in this example was in principle the same as that described in example 8. 200 mM 1,2,4- oxodiazolidine-2,5-dione were used instead of thiophenol. For this reaction, the cells were permeabilized by treating them with 10% chloroform. After a reaction time of 30 min, using cells corresponding to an activity of 72 units/ml in the mixture, the conversion was determined to be 11%.

Accordingly, while only several embodiments of the present invention have been shown and described, it is obvious that many changes and modifications may be made thereunto without departing from the spirit and scope of the invention.

What is claimed is:

1. A process for preparing a non-proteinogenic L-amino acid by an enzymic biotransformation comprising reacting O-acetyl-L-serine with a nucleophilic compound, while using an O-Acetyl-L-serine sulfhydrylase as catalyst; and carrying out the process at a pH in the range between pH 5.0 and 7.4 to produce the non-proteinogenic L-amino acid.

2. The process as claimed in claim 1, which is carried out at a pH in the range between pH 6.0 and 7.1.

3. A process for preparing a non-proteinogenic L-amino acid comprising reacting O-acetyl-L-serine with a nucleophilic compound, while using an O-Acetyl-L-serine sulfhydrylase as catalyst, wherein CysM is used as the O-acetyl-L-serine sulfhydrylase, and carrying out the process at a pH in the range between pH 5.0 and 7.4 to produce the non-proteinogenic L-amino acid.

4. The process as claimed in claim 1, wherein the O-acetyl-L-serine sulfhydrylase has a volume activity, $A_{cys}$, of at least 2 units/ml in the mixture.

5. A process for preparing a non-proteinogenic L-amino acid comprising reacting O-acetyl-L-serine with a nucleophilic compound, while using an O-Acetyl-L-serine sulfhydrylase as catalyst;

metering O-acetyl-L-serine, O-acetyl-L-serine sulfhydrylase and the nucleophilic compound in constantly and, at the same time, removing a solution containing the non-proteinogenic L-amino acid; and carrying out the process at a pH in the range between pH 5.0 and 7.4 to produce the non-proteinogenic L-amino acid.

6. The process as claimed in claim 1, wherein the O-acetyl-L-serine sulfhydrylase is used in purified form.

7. The process as claimed in claim 1, wherein the O-acetyl-L-serine sulfhydrylase is used after having been immobilized on a support.

8. A process for preparing a non-proteinogeflic L-amino acid comprising reacting O-acetyl-L-serine with a nucleophilic compound, while using an O-Acetyl-L-serine sulfhydrylase as catalyst;

wherein an O-Acetyl-L-serine-containing fermenter broth is used as the O-acetyl-L-serine; and carrying out the process at a pH in the range between pH 5.0 and 7.4 to produce the non-proteinogenic L-amino acid.

9. The process as claimed in claim 1, wherein the O-acetyl-L-serine sulfhydrylase is used in the form of resting microorganism cells which possess an O-Acetyl-L-serine sulfhydrylase activity.

10. The process as claimed in claim 1, wherein the nucleophilic compound contains a radical selected from the group consisting of -continued 11. The process as claimed in claim 10, wherein the nucleophilic compound is selected from the group consisting of the thiosulfates, of the thiols of the formula (1):

$$H\!-\!S\!-\!R^1 \qquad (1)$$

where $R^1$ is a monovalent substituted or unsubstituted alkyl, alkoxy, aryl or heteroaryl radical having from 1 to 15 C atoms, of the selenides, of the selenols of the formula (2)

$$H\!-\!Se\!-\!R^1 \qquad (2)$$

where $R^1$ has the meaning given for formula (1), of the azides, of the cyanides, of the azoles of the formula (3) or (4):

where X and Y are identical or different and are $CR^4$ or N, and $R^4$ is —H, —COOH, —OH, —NH$_2$, —NO$_2$—, —SH, —SO$_3^-$, —F, —Cl, —Br, —I, $C_1$–$C_5$-alkylcarbonyl- and also their esters, amides or salts, or $R^1$, and $R^1$ has the meaning given for formula (1), and where $R^2$ and $R^3$ are identical or different and are $R^4$ or where $C^1$ and $C^2$ in formula (4) are linked, in place of the substituents $R^2$ and $R^3$, by means of a bridge $[\!-\!CR^5R^6\!-\!]_a$, where a is 1, 2, 3 or 4, to form a ring, where $R^5$ and $R^6$ are identical or different and are $R^4$, and one or more non-adjacent groups $[\!-\!CR^5R^6\!-\!]$ can be replaced with oxygen, sulfur or an imino radical which is optionally substituted by $C_1$–$C_5$-alkyl, and two adjacent groups $[\!-\!CR^5R^6\!-\!]$ can be replaced with a group $[\!-\!CR^5\!=\!CR_6\!-\!]$ or with a group $[\!-\!CR^5\!=\!N\!-\!]$, of the isoxazolinones of the formula (5) or (6):

-continued (6)

where X, R¹, R² and R³ have the meaning which has already been given, and
where C¹ and C² in formula (6) can be linked, in place of the substituents R² and R³, by means of a bridge as defined for formula (4) to form a ring.

12. The process as claimed in claim 10, wherein the nucleophilic compound is selected from the group consisting of 2-mercaptoethanol, 3-mercaptopropanol, 3-mercaptopropionic acid, 3-mercapto-1-propanesulfonic acid, mercaptoethanesulfonic acid, 2-mercaptoethylamine, thioglycolic acid, thiolactic acid, thioacetic acid, mercaptosuccinic acid, mercaptopyruvic acid, dithiothreitol, dithioerythritol, 1-thioglycerol, thiophenol, 4-fluorothiophenol, 4-chlorothiophenol, 4-mercaptophenol, p-thiocresol, 5-thio-2-nitrobenzoic acid, 2-mercaptothiazole, 2-mercaptothiazoline, 2-mercaptoimidazole, 3-mercapto-1,2,4-triazole, 2-thiophenethiol, 2-mercaptopyridine, 2-mercaptopyrimidine, 2-thiocytosine, 2-mercaptonicotinic acid, 2-mercapto-1-methylimidazole, 2-mercaptobenzothiazole, 2-mercaptobenzoxazole, 6-mercaptopurine, sodium thiosulfate, potassium thiosulfate, ammonium thiosulfate, sodium azide, potassium azide, ammonium azide, potassium cyanide, sodium cyanide, ammonium cyanide, methylselenol, ethylselenol, propylselenol, phenylselenol, 1,2-pyrazole, 3-methylpyrazole, 4-methylpyrazole, 3,5-dimethylpyrazole, 3-aminopyrazole, 4-amino-pyrazole, pyrazole-4-carboxylic acid, pyrazole-3,5-dicarboxylic acid, 1,2,3-triazole, 1,2,4-triazole, 3-amino-1,2,4-triazole, 1,2,3,4-tetrazole, indazole, indazole-3-carboxylic acid, indazole-5-carboxylic acid, 5-aminoindazole, benzotriazole, benzotriazole-5-carboxylic acid, 5-aminobenzotriazole, aminopyrazolopyrimidine, 8-azaguanine, 8-azaadenine, isoxazolin-5-one, 3-methylisoxazolin-5-one, 4-methylisoxazolin-5-one, 4,5-dimethylisoxazolin-2-one and 1,2,4-oxadiazolidine-3,5-dione.

13. The process as claimed in claim 1,
wherein the nucleophilic compound has a concentration such that the compound is present in a concentration which is equimolar with that of O-acetyl-L-serine.

14. The process as claimed in claim 1, comprising carrying out the process at a temperature between 5° C. and 70° C.

15. The process as claimed in claim 1,
wherein the unnatural L-amino acid is selected from the group of the amino acids consisting of the formula (7) in the L configuration (7)

where Z is a monovalent radical in accordance with one of the formulae (8) to (19)

$$—S—SO_3^-,$$ (8)

$$—S—R^1,$$ (9)

$$—Se—H,$$ (10)

$$—Se—R^1,$$ (11)

$$—N=N^+=N^-,$$ (12)

$$—C\equiv N,$$ (13)

(14)

(15)

(16)

(17)

(18)

(19)

and the esters, ethers or salts thereof,
and R¹, R², R³, R⁴, X and Y have the meaning given for the formulae (1) to (6).

16. The process as claimed in claim 1, further comprising isolating the non-proteinogenic L-amino acid after the process has been terminated.

17. The process as claimed in claim 16, wherein the isolation is by means of a step selected from the group consisting of filtration, centrifugation, extraction, adsorption, ion exchange chromatography, precipitation and crystallization.

18. The process as claimed in claim 1, which is carried out at a pH in the range between pH 6.0 and 6.99.

19. The process as claimed in claim 3, which is carried out at a pH in the range between pH 6.0 and 7.1.

20. The process as claimed in claim 3, which is carried out at a pH in the range between pH 6.0 and 6.99.

21. The process as claimed in claim 5, which is carried out at a pH in the range between pH 6.0 and 7.1.

22. The process as claimed in claim 5, which is carried out at a pH in the range between pH 6.0 and 6.99.

23. The process as claimed in claim 8, which is carried out at a pH in the range between pH 6.0 and 7.1.

24. The process as claimed in claim 8, which is carried out at a pH in the range between pH 6.0 and 6.99.

* * * * *